United States Patent [19]

Levine et al.

[11] 4,258,223

[45] Mar. 24, 1981

[54] PROCESS FOR THE PREPARATION OF TERTIARY BUTYL ALCOHOL

[75] Inventors: Ralph Levine, Freehold; Jerome R. Olechowski, Lawrenceville, both of N.J.

[73] Assignee: Cities Service Company, Tulsa, Okla.

[21] Appl. No.: 932,090

[22] Filed: Aug. 8, 1978

[51] Int. Cl.³ .............................................. C07C 29/04
[52] U.S. Cl. ................................................... 568/899
[58] Field of Search .......................................... 568/899

[56] References Cited

U.S. PATENT DOCUMENTS 2,106,521   1/1938   Deanesly ............................. 568/899

Primary Examiner—Joseph E. Evans
Attorney, Agent, or Firm—Donald L. Traut; Patricia J. Hogan

[57] ABSTRACT

A process for the recovery of isobutylene as tertiary butyl alcohol from a stream of $C_4$ hydrocarbons comprising contacting the stream with an aqueous acid solution comprising from 50 to 80 wt % hydrocarbyl sulfonic acid, recovering from the resultant mixture an aqueous acid phase containing tertiary butyl alcohol and recovering from the acid phase the product tertiary butyl alcohol.

10 Claims, 1 Drawing Figure

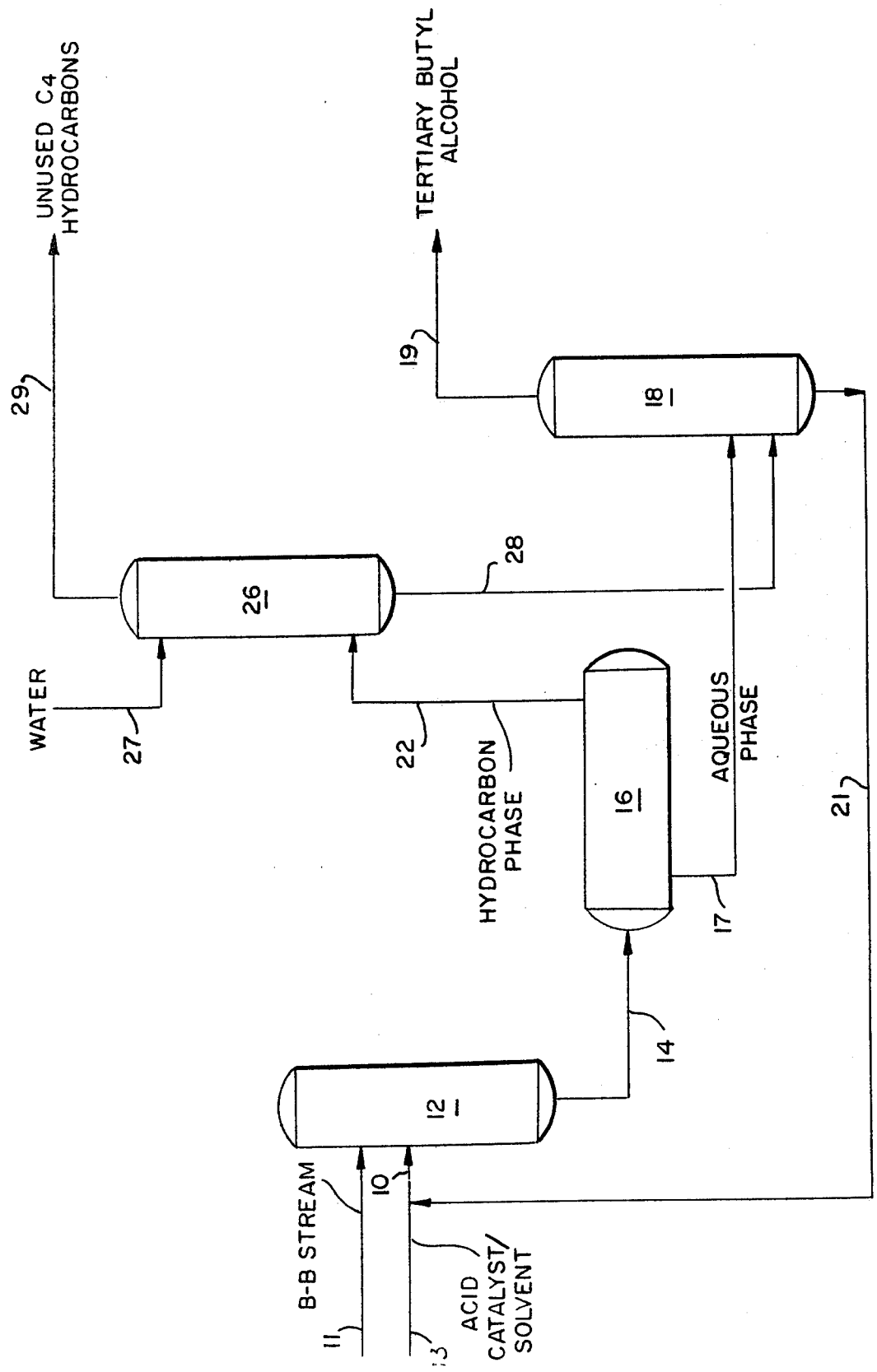

PROCESS FOR THE PREPARATION OF TERTIARY BUTYL ALCOHOL

BACKGROUND OF THE INVENTION

The present invention relates to a process for the recovery of isobutylene as tertiary butyl alcohol from a stream of $C_4$ hydrocarbons. More particularly, it involves a process for removing selectively isobutylene in the form of tertiary butyl alcohol using a hydrocarbyl sulfonic acid catalyst solvent.

Processes for recovery of isobutylene as tertiary butyl alcohol from a $C_4$ stream of hydrocarbons are known. Prior art references include U.S. Pat. Nos. 2,968,682, 3,300,539, 3,231,632, and 3,657,374 (Class 260-677A) which are hereby incorporated by reference.

Typically, under U.S. Pat. Nos. 2,968,682 and 3,300,539 these processes have contacted a BB stream containing isobutylene with an aqueous sulfuric acid mixture, the isobutylene being selectively absorbed and reacted to form tertiary butyl alcohol. The processes have separated from the resultant mixture an aqueous phase containing sulfuric acid, water and tertiary butyl alcohol. The processes then heat the aqueous phase to dehydrate the tertiary butyl alcohol and separate isobutylene from the acid phase.

The concentration of sulfuric acid in the aqueous catalyst solvent in '682 is between about 40 and 65% and the reaction temperature employed varies between $-15°$ C. and $+40°$ C. In '539, the sulfuric acid catalyst/solvent comprises between about 40 and 75 wt % acid with a reaction temperature between $-7°$ and $38°$ C.

Under U.S. Pat. No. 3,657,374, the process utilizes an aqueous catalyst solvent comprising from 30 to 45 wt % sulfuric acid and 2 to 25 wt % tertiary butyl alcohol in place of the sulfuric acid solution of '682 and '539. The process recovers an aqueous acid phase from the resultant mixture. Subsequently the process recovers tertiary butyl alcohol from the acid phase. The methods described above using sulfuric acid are highly corrosive to process equipment.

Under U.S. Pat. No. 3,321,632, the process uses toluene sulfonic acid as a catalyst/solvent in the esterfication of iso-olefins with lower alkanoic acids. The process comprises contacting $C_4$ hydrocarbon vapor with an acid solution consisting of 85 to 99 wt % lower alkanoic acid and 1 to 15% strong acid (sulfuric acid, toluene sulfonic acid, etc.) at a temperature between about $20°$ C. and $50°$ C.

Additionally the prior art includes an article by F. G. Ciapetta and M. Kilpatrick, *J. Am. Chem. Soc.*, Vol. 70, pp. 639-46 (1948) which discloses hydration of isobutylene in the presence of para-toluene sulfonic acid. Ciapetta teaches an acid concentration of between 0.8 and 7.6% and hydration temperatures of $25°$ and $35°$ C.

SUMMARY OF THE INVENTION

It is therefore an object of the present invention to set forth a process for the preparation of tertiary butyl alcohol from a stream containing isobutylene.

It is still further the object of the present invention to prepare the tertiary butyl alcohol using a less corrosive acid.

Other and further objects and advantages of the present invention will become more apparent hereinafter.

In accordance with the present invention, the process for preparing tertiary butyl alcohol comprises contacting the $C_4$ hydrocarbon stream with an aqueous acid solution comprising from about 50% to about 80% hydrocarbyl sulfonic acid in a reaction zone at a temperature between about $10°$ to about $80°$ C., whereby tertiary butyl alcohol is formed. The resulting acidic mixture is allowed to separate into a hydrocarbon phase and an aqueous phase comprising tertiary butyl alcohol, water and hydrocarbyl sulfonic acid. The tertiary butyl alcohol product is recovered from the separated aqueous phase.

DETAILED DESCRIPTION OF THE INVENTION

The process of the invention for the preparation of tertiary butyl alcohol from a B—B stream is exemplified in the accompanying flow diagram which is described in detail as follows:

A B—B stream obtained from a thermal cracking process and containing about 56 weight percent isobutylene, 5 weight percent of a mixture of n- and iso-butanes and 38 weight percent n-butenes is introduced through a line 11 into a reaction zone 12. A 63 weight percent para-toluene sulfonic acid aqueous solution, which functions as both solvent and catalyst, is introduced into the reaction zone 12 through a line 13. Extraction of the isobutylene component of the B—B stream by the para-toluene sulfonic acid and hydration of the isobutylene to form tertiary butyl alcohol is effected in the reaction zone 12 with an acid to isobutylene ratio of 3:1. The hydration reaction is effected at a temperature between about $10°$ and $80°$ C.

There is withdrawn from the reaction zone 12 through line 14, a reaction mixture comprising tertiary butyl alcohol, excess water, para-toluene sulfonic acid and unreacted $C_4$ liquids. This mixture is introduced into a separator 16 wherein the aqueous acid phase is allowed to separate from unreacted $C_4$ phase. The acid phase comprising tertiary butyl alcohol, water, para-toluene sulfonic acid, and trace $C_4$ hydrocarbons is withdrawn from the separator 16 through a line 17.

The acid phase is introduced into a distillation column 18. The temperature of the overhead is maintained at about $55°$ C. and the bottoms temperature is about $77°$ C. The pressure of the column is maintained between about 150 and 300 mm of Hg. An aqueous solution containing about 80 to 88 wt % tertiary butyl alcohol is obtained as an overhead fraction from the column 18 through line 19 and can be used as such or in dehydration processes well known in the art.

An aqueous solution comprising about 63 wt % para-toluene sulfonic acid and 2 to 5% tertiary butyl alcohol is obtained as a bottoms residue from the column 18 through line 21 and is returned to the acid inlet line 10.

The unreacted $C_4$ hydrocarbon phase comprising n- and isobutane, n-butenes, isobutylene and tertiary butyl alcohol, is removed from the separator 16 through a line 22. This $C_4$ phase is introduced into a water wash tower 26 for removal of the remaining tertiary butyl alcohol. Wash water is added via line 27 to the top of wash tower 26. After contacting the hydrocarbon phase, the wash water containing tertiary butyl alcohol is withdrawn from the wash tower 26 through line 28 and introduced into the distillation column 18. $C_4$ hydrocarbons, washed of tertiary butyl alcohol, are withdrawn through line 29.

In another embodiment of the present invention, the wash water containing tertiary butyl alcohol may be introduced into the separator 16.

Optionally, the aqueous phase withdrawn from the separator 16 is introduced into a debutanizing column (not shown). A debutanized aqueous phase comprising tertiary butyl alcohol, water and para-toluene sulfonic acid is withdrawn as a column bottoms and introduced to the distillation column 18. An wet $C_4$ overhead fraction is withdrawn from the debutanizing column, condensed and combined with the unreacted $C_4$ liquids removed from the separator 16 and introduced into the wash tower 26.

The stream of $C_4$ hydrocarbons employed in the process of the invention is normally obtained as a by-product of a refinery process such as catalytic cracking, thermal cracking, and catalytic reforming.

A typical $C_4$ hydrocarbon stream obtained as a by-product of a thermal cracking of naphtha comprises 4.7% n- and isobutanes, 25.6% isobutylenes, 24.9% n-butenes, and 43.7% butadiene. A typical $C_4$ hydrocarbon stream obtained as a by-product of a fluid catalytic cracking process comprises 1.4% $C_3$, 36.8% n- and isobutanes, 8.4% isobutylene, 29.7% n-butenes, 0.2% butadiene, 23.5% $C_5$ and 0.3% $C_6$. A mixture of $C_4$ hydrocarbons usually called a B—B stream obtained from a refinery process or a blend of $C_4$ hydrocarbon mixtures from different refining processes is employed in the process of this invention.

The stream should contain at least 8% isobutylene (calculated on a $C_4$ hydrocarbon stream basis) and have a sulfur concentration of less than 100 parts per million (calculated on an isobutylene basis). Preferably, the concentration of the stream should be at least 25% isobutylene and have less than 50 ppm sulfur. More preferably, the stream concentration of sulfur should be less than 10 ppm. Most preferably, the sulfur concentration should be less than 5 ppm.

The acidic solvent/catalyst is an aqueous solution of a hydrocarbyl sulfonic acid. The solution comprises from about 50 to about 80 wt % of a hydrocarbyl sulfonic acid. Below an acid concentration of 50%, the reaction activity falls off dramatically. Preferably, the solution comprises from about 60 to about 72 wt % hydrocarbyl sulfonic acid. Above a 72 wt % concentration, solid toluene sulfonic acid monohydrate precipitates from the solution at 30° C. However, a solution comprising a wt % above 72% para-toluene sulfonic acid can be employed, if the acid solution comprises additionally a small percentage of tertiary butyl alcohol, i.e. 2 to 3 wt % or the temperature of the reaction zone and acid solution is maintained in excess of 30° C. More preferably, the solution comprises about 63 wt % para-toluene sulfonic acid.

The solvent catalyst for the hydration reaction is a hydrocarbyl sulfonic acid. By "hydrocarbyl" is meant alkyl, alkenyl, cycloalkyl, aryl, alkaryl, and similar moieties. Specific examples which are of particular utility and are preferred are benzene sulfonic acid, methane sulfonic acid and toluenesulfonic acid. The more preferred sulfonic acid is toluene sulfonic acid (specifically para-toluene sulfonic acid).

Also as a preferred embodiment, the solvent/catalyst may comprise a mixture of two or more hydrocarbyl sulfonic acids. An example of one such mixture is para-toluene sulfonic acid and ortho-toluene sulfonic acid. Broadly, however, any sulfonic acid or combination of acids which are useful as an hydration catalyst/solvent can be employed as a component of the present invention.

The hydration reaction is effected at a temperature between about 10° and about 80° C. Preferably, the hydration reaction temperature is between about 30° and 50° C.

Preferably, the pressure range selected for the extraction zone is sufficient to maintain an essentially liquid phase operation in the extraction zone and of course varies with the temperature level maintained in the extraction zone. More preferably, the pressure range is maintained between about one half to about 2 atmospheres above the vapor pressure of the B—B stream. The maintenance of liquid phase conditions in the extraction/reaction step coupled with the judicious selection of temperatures and pressures falling within the above broad ranges assures the intimate contact of the B—B stream with the solvent catalyst solution.

Although liquid phase is preferred, as indicated previously, the tertiary butyl alcohol forming reaction can be effected in the reaction zone 12 by the passage of a vapor B—B stream through the liquid solvent catalyst. A lower pressure would be required to maintain the vapor B—B stream.

The contact time in the reaction zone of either the liquid/liquid or gas/liquid system is dependent upon the composition of feed, i.e. % isobutylene and ppm sulfur and the % conversion of isobutylene to tertiary butyl alcohol desired and is not critical. Preferably, the contact times between about 5 minutes to about 20 hours will give good results. More preferred, the contact time varies from 15 minutes to 60 minutes.

The acid solvent/catalyst to isobutylene weight ratio ranges from about 1:1 to about 10:1. Preferably, the acid to isobutylene ratio ranges from about 2.5:1 to about 5.2:1. More preferably, the acid to isobutylene ratio is 3.5:1.

The reaction zone 12 may comprise a batch reactor, a concurrent flow reactor, a countercurrent flow reactor or any other physical method of contacting one liquid phase stream with a gas/liquid phase stream. It is envisioned that in the case of a countercurrent flow reactor, a separator would not be necessary.

The pressure of the distillation step is not critical but it is preferred to have a pressure below that which is maintained in the reaction zone. The pressure can vary between 50 mm of Hg and 3 atmospheres, but is preferably between 150 and 300 mm of Hg.

In order that those skilled in the art may more completely understand the present invention and the preferred methods by which the same may be carried into effect, the following examples are offered.

EXAMPLE 1

A mixture having various acid to isobutylene ratios was charged to a one gallon autoclave fitted with a two inch, six bladed turbine. The mixture comprised a B—B stream mixture generally containing:

| | |
|---|---|
| Propylene | 0.48% |
| Propane | 0.94% |
| Isobutane | 26.0% |
| n-Butane | 10.87% |
| Isobutylene | 8.4% |
| Butene-1 | 8.82% |
| trans-Butene-2 | 12.14% |
| 1,3-Butadiene | 0.22% |
| cis-Butene-2 | 8.8% |
| Total $C_5$ olefins | 23.5% |
| $C_6+$ | 0.34% | and an aqueous solution of 63% para-toluene sulfonic acid. The auto clave and contents were sealed and maintained at various temperatures. The mixture was stirred at a rate of 1500 r.p.m. At various times, the aqueous phase was analyzed for tertiary butyl alcohol as determined by infrared spectraphotometry. The unreacted $C_4$ phase was analyzed for isobutylene as determined by vapor phase chromatography. The yields are presented in Table A below.

TABLE A

| Time, hr | Temp. °C. | % PTSA | Acid/CH | % iC$_4$ in Feed | %iC$_4$ Extracted |
|---|---|---|---|---|---|
| 2.0 | 20 | 45 | 3.9 | 16.40 | 1.6 |
| 18.0 | 20 | 45 | 2.8 | 16.40 | 8.6 |
| 3.0 | 40 | 45 | 5.7 | 16.15 | 66.38 |
| 3.0 | 40 | 45 | 5.7 | 17.66 | 94.28 |
| 1.0 | 50 | 45 | 12.5 | 7.31 | 62.38 |
| 3.0 | 50 | 45 | 5.0 | 19.60 | 81.17 |
| 4.0 | 50 | 45 | 1.9 | 17.66 | 89.47 |
| 0.5 | 30 | 63 | 4.1 | 8.29 | 63.34 |
| 0.5 | 30 | 63 | 4.3 | 8.29 | 90.67 |
| 0.5 | 30 | 63 | 4.1 | 8.29 | 90.83 |
| 1.0 | 30 | 63 | 4.1 | 8.29 | 54.35 |
| 1.0 | 30 | 63 | 4.1 | 8.29 | 80.94 |

EXAMPLE 2

An aqueous solution of 59.0% toluene sulfonic acid was combined with a hydrocarbon mixture containing the following

| | |
|---|---|
| n-Butane | 5% |
| Isobutylene | 56% |
| Butene-1 | 25% |
| trans-Butene-2 | 10% |
| 1,3 Butadiene | 1% |
| cis-Butene-2 | 1% |
| Misc. | 2% | in an acid to isobutylene ratio of 3.5:1 in an autoclave fitted with a six blade turbine. The autoclave and contents were sealed and maintained at 40° C. The mixture was stirred at a rate of 1500 r.p.m. At various times, the unreacted $C_4$ phase was analyzed for isobutylene as determined by vapor phase chromatography. The yields are presented in Table B below.

TABLE B

| Time, min | Isobutylene Extracted, % |
|---|---|
| 30 | 19.5 |
| 60 | 80.5 |

EXAMPLE 3

Example 2 was repeated with an aqueous solution of 61.3% para-toluene sulfonic acid. Results are shown in Table C below.

TABLE C

| Time, min | Isobutylene Extracted, % |
|---|---|
| 30 | 78.3 |
| 60 | 92.5 |

EXAMPLE 4

Example 2 was repeated with an aqueous solution of 63.3% para-toluene sulfonic acid. Results are shown in Table D below.

TABLE D

| Time, min | Isobutylene Extracted, % |
|---|---|
| 30 | 83.2 |
| 60 | 94.0 |

EXAMPLE 5

Example 2 was repeated with an aqueous solution of 64.7% para-toluene sulfonic acid. Results are shown in Table E below.

TABLE E

| Time, min | Isobutylene Extracted, % |
|---|---|
| 30 | 87.5 |
| 60 | 94.6 |

EXAMPLE 6

Example 2 was repeated with an aqueous solution of 67.0% para-toluene sulfonic acid. Results are shown in Table F below.

TABLE F

| Time, min | Isobutylene Extracted, % |
|---|---|
| 30 | 91.9 |
| 60 | 95.6 |

EXAMPLE 7

Example 2 was repeated with an aqueous solution of 71.4% para-toluene sulfonic acid. Results are shown in Table G below.

TABLE G

| Time, min | Isobutylene Extracted, % |
|---|---|
| 15 | 94.5 |
| 30 | 95.5 |
| 60 | 96.2 |

EXAMPLE 8

Example 2 was repeated with an aqueous solution of 69.7% para-toluene sulfonic acid. Results are shown in Table H below.

TABLE H

| Time, min | Isobutylene Extracted, % |
|---|---|
| 15 | 92.4 |
| 30 | 95. |
| 60 | 96. |

We claim:
1. A process which comprises:
(a) contacting a $C_4$ hydrocarbon stream containing at least about 8% by weight of isobutylene and less than about 100 ppm sulfur in a reaction zone at a temperature of about 10°–80° C. with an aqueous acid solution comprising about 50–80% by weight of an aryl or alkaryl sulfonic acid in such proportions as to provide about 1–10 parts by weight of acid solution per part by weight of isobutylene, (b) recovering from the resultant reaction mixture an aqueous phase comprising t-butyl alcohol, water, and hydrocarbyl sulfonic acid, and (c) recovering t-butyl alcohol from the aqueous phase.

2. The process of claim 1 wherein the acid solution to isobutylene ratio is between about 2.5:1 and 5.2:1.

3. The process of claim 1 wherein said $C_4$ hydrocarbon stream comprises at least about 25 weight % isobutylene and less than about 10 ppm sulfur.

4. The process of claim 1 wherein said reaction zone is maintained in the liquid phase.

5. The process of claim 1 wherein said reaction zone is maintained at a temperature of between about 30° to about 50° C.

6. The process of claim 1 wherein said sulfonic acid is selected from a group comprising benzene sulfonic acid and alkyl benzene sulfonic acid.

7. The process of claim 6 wherein said sulfonic acid is para-toluene sulfonic acid.

8. The process of claim 7 wherein the aqueous acid solution comprises from about 60 to about 70 weight % para-toluene sulfonic acid.

9. The process of claim 1 which comprises:
(a) contacting a $C_4$ hydrocarbon stream containing at least about 25% by weight of isobutylene and less than about 10 ppm sulfur in a reaction zone at a temperature of about 30°–50° C. with an aqueous acid solution comprising about 60–70% by weight of p-toluenesulfonic acid in such proportions as to provide about 2.5–5.2 parts by weight of acid solution per part by weight of isobutylene,
(b) allowing the resultant reaction mixture to separate into an aqueous phase comprising t-butyl alcohol, water, and p-toluenesulfonic acid and a hydrocarbon phase comprising unreacted $C_4$ hydrocarbons and t-butyl alcohol in a separator,
(c) distilling the separated aqueous phase in a distillation column to provide an aqueous solution of t-butyl alcohol as an overhead fraction and an aqueous solution of p-toluenesulfonic acid and t-butyl alcohol as a bottoms residue,
(d) returning the bottoms residue to the reaction zone, and
(e) washing the separated hydrocarbon phase of step (b) in a water wash tower to separate a $C_4$ hydrocarbon phase and a wash water phase containing t-butyl alcohol and introducing the wash water phase into the distillation column of step (c).

10. The process of claim 1 which comprises:
(a) contacting a $C_4$ hydrocarbon stream containing at least about 25% by weight of isobutylene and less than about 10 ppm sulfur in a reaction zone at a temperature of about 30°–50° C. with an aqueous acid solution comprising about 60–70% by weight of p-toluenesulfonic acid in such proportions as to provide about 2.5–5.2 parts by weight of acid solution per part by weight of isobutylene,
(b) allowing the resultant reaction mixture to separate into an aqueous phase comprising t-butyl alcohol, water, and p-toluenesulfonic acid and a hydrocarbon phase comprising unreacted $C_4$ hydrocarbons and t-butyl alcohol in a separator,
(c) distilling the separated aqueous phase in a distillation column to provide an aqueous solution of t-butyl alcohol as an overhead fraction and an aqueous solution of p-toluenesulfonic acid and t-butyl alcohol as a bottoms residue,
(d) returning the bottoms residue to the reaction zone, and
(e) washing the separated hydrocarbon phase of step (b) in a water wash tower to separate a $C_4$ hydrocarbon phase and a wash water phase containing t-butyl alcohol and introducing the wash water phase into the separator of step (b).

* * * * *